(12) United States Patent
Struillou et al.

(10) Patent No.: US 8,242,069 B2
(45) Date of Patent: Aug. 14, 2012

(54) NEAR ANHYDROUS CONSUMER PRODUCTS COMPRISING FRAGRANCED AMINOPLAST CAPSULES

(75) Inventors: Arnaud Struillou, Archamps (FR);
Claudie Bellouard Drevet, La Roche sur Foron (FR); Lahoussine Ouali, Vetraz-Monthoux (FR); Glenn Verhovnik, Chene-Bougeries (CH)

(73) Assignee: Firmenich SA, Geneva (CH)

( * ) Notice: Subject to any disclaimer, the term of this patent is extended or adjusted under 35 U.S.C. 154(b) by 263 days.

(21) Appl. No.: 11/915,723

(22) PCT Filed: May 31, 2006

(86) PCT No.: PCT/IB2006/051729
§ 371 (c)(1),
(2), (4) Date: Nov. 27, 2007

(87) PCT Pub. No.: WO2006/131846
PCT Pub. Date: Dec. 14, 2006

(65) Prior Publication Data
US 2008/0227675 A1    Sep. 18, 2008

(30) Foreign Application Priority Data
Jun. 8, 2005 (EP) .................................... 05105027

(51) Int. Cl.
*C11D 17/04* (2006.01)
(52) U.S. Cl. ........................................ 510/441
(58) Field of Classification Search ............... 510/441
See application file for complete search history.

(56) References Cited

U.S. PATENT DOCUMENTS

| 4,145,184 A | 3/1979 | Brain et al. ................ 8/137 |
| 5,324,444 A | 6/1994 | Berry et al. ............ 252/174.11 |
| 6,194,375 B1 | 2/2001 | Ness et al. ................. 512/4 |
| 2003/0148908 A1* | 8/2003 | Michel et al. .............. 510/296 |
| 2004/0087477 A1 | 5/2004 | Ness ........................ 512/4 |
| 2004/0138093 A1 | 7/2004 | Brain et al. ................ 512/4 |
| 2004/0142840 A1 | 7/2004 | De Buzzaccarini et al. .. 510/296 |
| 2005/0112152 A1* | 5/2005 | Popplewell et al. ......... 424/401 |

FOREIGN PATENT DOCUMENTS

| EP | 0 381 261 A1 | 8/1990 |
| EP | 0 397 246 B1 | 3/1995 |
| EP | 1 407 753 A1 | 4/2004 |
| EP | 1462 514 A1 | 9/2004 |
| EP | 1 400 460 B1 | 11/2004 |
| GB | 1 008 016 | 10/1965 |
| GB | 1 455 283 | 11/1976 |
| WO | WO 93/13195 | 7/1993 |
| WO | WO 98/28296 | 7/1998 |
| WO | WO 00/66704 | 11/2000 |
| WO | WO 01/51197 A1 | 7/2001 |
| WO | WO 01/62376 A1 | 8/2001 |
| WO | WO 02/074430 A1 | 9/2002 |
| WO | WO 02/102955 A1 | 12/2002 |
| WO | WO 03/010266 A1 | 2/2003 |
| WO | WO 03/089561 A2 | 10/2003 |
| WO | WO 2004/011585 A1 | 2/2004 |
| WO | WO 2004/011586 A1 | 2/2004 |
| WO | WO 2005/017085 A1 | 2/2005 |

OTHER PUBLICATIONS

International Search Report for PCT/IB2006/051729.

* cited by examiner

*Primary Examiner* — John Hardee
(74) *Attorney, Agent, or Firm* — Winston & Strawn LLP

(57) ABSTRACT

A liquid substantially non-aqueous cleaning or conditioning composition containing a surfactant or a conditioning active ingredient, a content in water which is not above 10% by weight, relative to the total weight of the composition, and a fragrance encapsulated in aminoplast type microcapsules. The compositions of the invention, in the form of fabric detergents or softeners, are particularly stable during storage and have an improved olfactive impact on fabrics.

16 Claims, No Drawings

NEAR ANHYDROUS CONSUMER PRODUCTS COMPRISING FRAGRANCED AMINOPLAST CAPSULES

TECHNICAL FIELD

The present invention relates to the perfume and consumer product industries. It concerns more particularly liquid consumer products comprising fragranced aminoplast capsules, in particular fragranced melamine resin microcapsules, wherein said microcapsules have been found to be particularly stable. The invention relates more particularly to near anhydrous liquid detergent and conditioner products comprising encapsulated perfumes which are perfectly stable therein, in spite of the high concentrations in surfactant which are characteristic of such non-aqueous liquid consumer products.

BACKGROUND ART

Cleaning, namely detergent, products in liquid form are often of a more convenient use than granular, powder products because they can be formulated in concentrated form and can be easily dissolved in the washing water of fabric or dishwashing machines. In spite of this, liquid detergents have limitations related to the stability of certain ingredients which are commonly used in detergents and softeners.

Liquid detergents are normally either isotropic liquids or structured liquids. They are mostly formed of combinations of anionic surfactants (linear alkylbenzenesulfonate, alkylsulfate, alkylsulfonate), soaps, non-ionic surfactants (alkyl ethoxylate, alkylpolyglucoside, sorbitan esters), builders (citrate, soap, sodium tripolyphosphate, zeolite), antifoam agents (silicone) and optionally combinations of various enzymes. All such consumer product bases contain perfume, typically in the range of at least 0.1 to 1% by weight, of the weight of consumer product. Some bases, in particular isotropic liquids, contain a significant concentration of hydrotrope such as 1,2-propanediol, glycerol, triethanolamine, diethanolamine, monoethanolamine and ethanol.

All liquid detergents contain large concentrations of surfactants (10-60% by weight) and typically water (40-80% of the total formula). They can be found on the market mainly in two formats, the so-called "regular" formulations (typically 10-25% by weight of surfactant content) and "concentrates" (typically 25-50% surfactant content). Typical examples of such formulations can be found for example in the textbook "Formulating detergents and personal care products" by Louis Ho Tan Tai, 2000, pages 156 to 172.

Liquid fabric-softeners typically contain high levels of softening agents with low levels of additives such as calcium chloride, fatty acids, non-ionic surfactants, ethanol, isopropanol, polyethylene glycol. Most commonly used softener actives are twin chains of cationic surfactants such as salts of distearyldimethylammonium, quaternary dialkylimidazolines and, in more recent products, diester quats such as those described in detail in US patent Application 2002/0011584 A, to S.C. Johnson & Sons, for example. Commercial fabric-softeners can be found mainly in two formats, the "regular" formulations (typically 3-10% by weight of softening active content) or "concentrates" (typically 10-20% by weight of softening active content). Typical examples of such formulations are also described in detail in the textbook of Louis Ho Tan Tai above-cited, pages 174 to 185. Most fabric softeners contain a very high level of water, typically from 70 to 95% by weight of the formulation.

The perfume contained in liquid detergents and fabric-softeners is deposited on the fabrics through the wash cycle but is lost over time, upon drying of the washed fabrics and slow evaporation thereafter. In order to prolong the perfume perception by the user of laundered fabrics, it has been taught in the literature to control the release of said perfume by encapsulating it into microcapsules. One class of microcapsules particularly suitable for this aim is that of core-shell capsules made of an inner core of liquid perfume oil enclosed in a thin shell of a polymeric material. Polymeric shells made of the reaction products of an amine, typically selected from urea and melamine, with an aldehyde, typically selected from formaldehyde, acetaldehyde and glutaraldehyde, are very commonly used for this purpose as they withstand the washing cycle of the fabrics and are transferred in a relatively intact form onto the fabrics. Rubbing of the latter during use allows controlled release of the perfume for a longer period of time than would otherwise be the case if the fragrance was not encapsulated. The use of such microcapsules has already been described in EP 0 397 246 B1, to cite but one example, to achieve controlled release of perfume on fabrics washed with various cleaning products such as granular or liquid laundry detergents and fabric-softeners.

However, it has been found that in liquid laundry detergents and fabric softeners containing high levels of surfactants (>5%, cationic or anionic or non-ionic) and water (at least 30% wt), the stability of such capsules is relatively poor. Over time, the encapsulated perfume leaks out of the microcapsule and can be found as free, un-encapsulated perfume in the product. It is believed that this leakage is driven by the high surfactant level in these formulations. Such problems have been quite extensively outlined in the patent literature, of which one can cite by way of example International patent application WO 02/074430, to Quest International, which discusses the above-mentioned stability problems of aminoplast capsules in aqueous surfactant-containing products and suggests a solution based on the use, in the capsule shell, of a second polymer comprising a polymer or copolymer of one or more cyclic anhydrides.

Another example of the manner in which this problem can be obviated can be found in International publication WO 2005/017085, filed by the Applicant, which addresses the same problem and cites prior art examples of the ways in which such fragrance microcapsules can be improved to become more stable in high surfactant and/or softener content liquid products. To this date however, no solution has provided a liquid product of this type having a microcapsule shelf stability beyond 2 months at 45° C., i.e. under storage conditions that are encountered in many practical circumstances.

So, it is an implication from the prior art that the major problem with the use of aminoplast or aminoresin capsules in liquid detergent and fabric softener products is the fact that the perfumed capsules are unstable in such liquid formulations. The perfume gets extracted out/off the capsules by the surface active ingredients in the formulation.

Amongst the various types of liquid consumer products currently used for cleaning and/or treating and softening a great variety of surfaces such as skin, hair, hard surfaces such as tiles, windows, kitchen and bathroom surfaces, or yet fabrics, there exist the so-called anhydrous or non-aqueous formulations. These products, unlike what is the case with aqueous liquids, can also contain bleach.

In such anhydrous or non-aqueous liquid products, an hydrophilic organic solvent is used to replace water. The hydrophilic organic solvent used to replace water can be a water-soluble non-ionic polyoxyethylene-polyoxypropylene copolymer (such as in U.S. Pat. No. 3,169,930 or GB 1455283, to Witco Chemical Corp), a low molecular weight polyethylene glycol (such as in U.S. Pat. No. 4,929,380 to Henkel), a glycol ether, an ethanolamine, or a low molecular weight alcohol or amine.

The amount of water in these products is typically below 10%, by weight, more preferably below 5% by weight, and in any case much lower than in aqueous liquid detergents or fabric softeners which contain typically 50 to 90% by weight of water. Thus, it is understood here that, when talking of anhydrous, near anhydrous or non-aqueous liquid products, we mean by this a liquid product that does not have more than 10% by weight of free water content.

As cited above, unlike aqueous liquid detergents, anhydrous or non-aqueous liquid detergents can also contain bleach (such as suspended perborate, as described in U.S. Pat. No. 4,800,038 or U.S. Pat. No. 5,057,238, to Colgate-Palmolive, or percarbonate), bleach activators (such as TAED, sodium nonaoyloxybenzenesulfonate, N-acyl caprolactam, glyceryl triacetate, or diketones as described for example in U.S. Pat. No. 5,437,686, to Colgate-Palmolive), or a bleach catalyst (such as 1,4,7-triazacyclononane). The bleach system can also be a preformed organic peracid, $R^1$—COOOH, such as described in US 2001/0001786, to G. Scialla.

In anhydrous or non-aqueous fabric softeners, the softener active can typically be a salt of a quaternary ammonium or imidazolinium (such as in U.S. Pat. No. 4,851,141 to Colgate-Palmolive or US 2004/0142840 to Procter & Gamble), an amido-amine (such as in WO 2004011585 to Colgate-Palmolive), clay alone or in combination with an organic softener (as in WO 2004/011586 to Colgate-Palmolive), silicone (as in US 2004/0142841 to Procter & Gamble) or a combination of organic softeners (such as fatty alcohols, fatty acids and esters, long alkyl chain non-ionic surfactants).

Such anhydrous or non-aqueous formulations of liquid detergents or fabric softeners can be sold as liquids in bottles or packaged in water-soluble containers (one of the first examples is cited in US 2003/0148908 to J. Michel et al.). Recently, much attention has been given to the formulation of such water soluble packages or pouches, allowing for single unit dosage in particular, and the interested reader will find significant descriptions thereof in recent documents such as U.S. Pat. No. 6,492,315 and U.S. Pat. Nos. 6,495,503, 504 and 505 to Colgate-Palmolive, US 2004/0142840 and 841 to Procter & Gamble, WO 02/102955 to Unilever, EP 1 400460 B1 and EP 1 462 514 A1 to Unilever, US 2004/0209793 to D. Fregonese, and US 2003/0148908 to J. Michel et al., amongst others, as well as in the prior art specifically cited in these documents as being pertinent in this context.

Such containers are often made of a water-soluble film of polyvinyl alcohol. Several such products have been launched in Europe over the past three years, containing anhydrous or non-aqueous liquid detergents in polyvinyl alcohol sachets.

Despite the large amount of prior art related to the formulation and packaging of anhydrous detergent and softener products, there are very few reports of particular forms of fragrance carriage in these products for the treatment of fabrics, hard surfaces, skin or hair, making it possible to achieve long lasting perfume delivery from the fabrics or other surfaces treated therewith.

This clearly contrasts with the extensive descriptions of the use of fragranced microcapsules for this purpose in aqueous liquids or powder products of the same category, i.e. intended for the treatment of a variety of surfaces. The fact that anhydrous or non-aqueous liquid detergents or softeners typically contain a higher concentration of active ingredient (anionic and non-ionic surfactants in liquid detergent, softener active in fabric-softener) than their aqueous liquid detergents or fabric-softeners counterparts is not strange to this. One would in fact have expected the leakage of perfume from microcapsules incorporated in anhydrous liquid products to be even more extensive than what is the case with aqueous liquids, and therefore expect no perfume release improvement with anhydrous liquid products carrying encapsulated perfumes.

Yet, we have just established, very surprisingly in view of the prior art, that the use of particular aminoplast fragrance microcapsules in anhydrous liquid soaps/detergents and conditioners/softeners is not only efficient but unexpectedly useful and advantageous. Provided that the water content in the formulation is kept below 10%, and preferably below 5%, the surfactant level in this low water/anhydrous formulation can be very high and yet the microcapsules will still be significantly more stable than in similar, high-water formulations.

This is a totally unexpected result in view of the prior art accepted principles that fragranced aminoplast microcapsules are unstable in high surfactant or softener containing liquid consumer products. Furthermore, it makes it possible to effectively deliver perfume onto the surfaces treated with such non-aqueous consumer liquids, in particular bleach containing liquid products.

The prior art is totally silent with regard to this problem of improved fragrance delivery from non-aqueous liquids onto fabrics and other surfaces. Although there have been some reports of construction of stable particles for incorporation in liquid compositions, in particular in anhydrous liquids, they have mostly concerned the physical dispersion stability of the product, i.e. they have been intended to solve the problem of sedimentation or agglomeration of particles containing the actives, which may lead to an inhomogeneous structure of the end product and thus reduced efficacy thereof. In this context, one can cite in particular U.S. Pat. No. 6,673,763 to Novozymes A/S and the prior art documents cited therein, namely on column 1, lines 49 to 60, as well as WO 00/066704 to Procter & Gamble.

To the best of our knowledge, these documents deal with either the encapsulation of detergent ingredients other than the perfume or they do not describe or suggest the use of fragrance aminoplast capsules in anhydrous liquid detergents or softeners.

Moreover, although US 2004/0142840 (hereinafter, the "840" document) and US 2004/0142841 (hereinafter, the "841" document) suggest that perfumes can be used in a form comprising a coating agent or a carrier (see respectively, §[0140] of "840" and §[0154] of "841"), this is clearly a general statement relating to the widely accepted use of encapsulated perfumes in laundry products in general and there is no specific teaching or suggestion that one could expect any particular advantage or improvement by using fragranced aminoplast capsules in particular in non-aqueous laundry treatment liquids. The inventors claim that they obtain more efficient deposition of the perfume with the unit dose fabric products disclosed, but this would appear to be related to the nature of the surfactant and softener system used, which is claimed to have improved cleaning and softening activity (see for example, the "Benefits" section, §[0243] of the "840" document, respectively [0243] of the "841" document).

In this context, one can also cite U.S. Pat. No. 5,480,575, to Lever Brothers, which proposes dissolving detergent reactive adjuncts in biopolymers. Although perfumes are cited as possible such adjuncts, there is no specific description or example of the manner in which perfumes might thus be encapsulated and incorporated in the non-aqueous liquid detergents which are the preferred object of this patent.

Finally, U.S. Pat. No. 6,194,375, to Quest International, discloses fragranced polymer particles suitable for incorporation into compositions comprising surfactants or active softening ingredients. The particles taught may be prepared from aminoplast resin microcapsules, but they carry on their exterior or within the capsule a further hydroxy-functional polymer, preferably highly hydrolysed polyvinyl alcohol. Although there is a general mention in this document (see column 10, line 18) that the taught particles can be used in liquids possibly having "a non-aqueous phase" (not clear what is effectively meant by this), all the examples relate to either solid products or to liquids having a high water content.

Despite the abundant literature existing on the preparation and use of aminoplast resin microcapsules, to the best of our knowledge, there is no prior art disclosure or suggestion of the present invention as herein claimed and advantageously used.

SUMMARY OF THE INVENTION

The present invention relates to the use of fragranced aminoplast microcapsules in non-aqueous or anhydrous liquid cleaning and conditioning compositions for the treatment of surfaces, fabric surfaces in particular.

It also relates to non-aqueous liquid soaps, detergents, softeners or conditioners, and more particularly to non-aqueous laundry and heavy duty liquid products, having a water content of 15% or less by weight, relative to the product weight, comprising such fragranced microcapsules. Preferred embodiments of the invention's liquid non-aqueous cleaning or conditioning compositions comprise less than 10% by weight of water, or even not more than 6% by weight, relative to the total weight of the compositions.

Surprisingly, it has been found that such capsules are quite stable in liquid laundry products having a very low water content and that they allow prolonged release of the perfume from the fabrics and other surfaces treated with such products. Moreover, depending on the microcapsules used, it may be possible to release the perfume by diffusion or via rubbing thereof and this advantageously renders such laundry products more versatile in their fabric perfuming efficacy.

The invention further concerns a method of treating fabrics or other surfaces, which comprises disposing the above-mentioned liquid detergent and/or softening products in the respective compartments of dish- or fabric-washing machines at the beginning of the wash cycle and contacting the fabrics or dishes with said product during the wash and/or rinse cycle. Alternatively, such methods comprise treating fabrics, kitchen or dish surfaces in a water environment with a detergent and/or conditioner as recited above.

The invention further provides packaged liquid products as recited, particularly in the form of single dosage units, packaged in water soluble carrier materials able to dissolve in water during the washing and/or rinsing of the fabrics or other surfaces to be treated with the non-aqueous liquid consumer products. The invention therefore also relates to a single dose unit of a non-aqueous liquid washing detergent or soap, and to a single dose unit of a non-aqueous liquid washing conditioner or softener, comprising fragranced aminoplast microcapsules.

DETAILED DESCRIPTION OF THE INVENTION

The invention relates to the use of fragranced aminoplast microcapsules in non-aqueous or anhydrous liquid detergents and conditioners for the treatment of surfaces, fabric surfaces in particular, and to the liquid products containing such microcapsules, provided that they do not contain more than 10% by weight of water or water based components.

We have surprisingly found that, provided that the amount of free water contained in these products remained within the limit cited above, the other components of the non-aqueous liquid rinse off product could be any of the currently used ingredients typically present in this type of products. A detailed description of the nature, function and dosage of such ingredients in non-aqueous type liquid detergents and softeners can be found in the very extensive body of patent literature available on the current products of this type.

We list below representative examples of such descriptions for each of these products and the contents of the cited documents relating to the formulation of the liquid detergent or softener are hereby included by reference. The skilled formulator of such products will have no difficulty incorporating the fragrance microcapsules of the invention, according to methods known per se and extensively described in the art for incorporating aminoplast capsules in laundry products, in the desired amount and so as to obtain a perfume delivery/perception from the treated surfaces, namely fabrics, that is prolonged over time.

The Non-Aqueous Liquid Detergents and Conditioners

For the purposes of the present invention, a "non-aqueous liquid cleaning or conditioning composition", namely a "non-aqueous liquid detergent or fabric softener", means here that the level of water or other aqueous component in the detergent or softener is 15% by weight or less, advantageously 10% by weight or less, more preferably not more than 6% by weight and even 3% by weight or less, relative to the total weight of the product.

Compositions which are compatible with this definition have been widely described in the prior literature. Their components and functions thereof are discussed in detail in many publications which are part of the patent literature. We list here-below a non-exhaustive number of representative examples, but the specialist will understand that no exhaustive list of such products can be covered here and that the cited examples cannot be taken to limit the scope of the invention.

The general principles of formulation of such products is also the object of the textbook by Ho Tai Tan previously cited, which constitutes a general source of information for laundry type formulations and the sections of which, dedicated to non-aqueous liquids, provide a useful source of reference.

Some of the earliest descriptions of non-aqueous liquid detergents can be found in GB 1008016 to Procter & Gamble, GB 1455283 to Witco Chemical Corp., U.S. Pat. No. 4,929, 380 to Henkel and EP 381 261 to Unilever and U.S. Pat. No. 4,800,035 and U.S. Pat. No. 5,057,238 to Colgate-Palmolive. The formulations contained in these document are perfectly compatible with the requirements of the compositions of the present invention and the contents of these documents pertaining to the formulations in question are hereby included by reference.

U.S. Pat. No. 5,872,092, to Procter & Gamble, relates to a bleach containing laundry detergent. A particularly complete description of the ingredients, composition, manner of formulating and production of a bleach-containing detergent can be found in this document, the contents of which are hereby included by reference.

Another representative example of liquid detergent compositions for laundry treatment, typically comprising no more than 5% weight of water, is that of U.S. Pat. No. 6,376,447, to Procter & Gamble, relating to an enzyme-containing detergent, or yet that of U.S. Pat. No. 6,576,602, assigned to the same company, which describes a surfactant-structured liquid phase detergent containing less than 5% weight of water. The pertinent teachings of these documents, relating to the ingredients and formulations of the liquid detergent bases, are hereby included by reference. U.S. Pat. No. 6,849,588 to Huntsman Petrochemical Corporation, also describes structured liquid detergents made with LAB sulfonates and useful to clean laundry and hard surfaces.

U.S. Pat. No. 5,437,686 to Colgate-Palmolive, previously cited, also describes a typical detergent formulation on column 7 which is compatible with the aims of the present invention. U.S. Pat. Nos. 4,800,035 and 5,057,238, owned by the same company, also cited previously, relate to liquid heavy-duty detergents, the composition of which is suitable for the purpose of the present invention.

Other examples of non-aqueous liquid detergent compositions can be found in the already cited U.S. Pat. No. 6,673,763, to Procter & Gamble, which deals with products comprising enzyme particles.

EP 1 400 514, and EP 1 462 514, assigned to Unilever, are further examples of non-aqueous laundry liquid detergents, in soluble package form. These documents teach in great detail both the composition of the detergent and the material and form of production of the single dosage pouches for their delivery an the teachings therein are hereby included by reference. A more recent publication of the same company, WO 03/010266, describes particular water-soluble polymers for the single dose packaging of non-aqueous detergents, the composition of which is also described in detail. All these detergent formulations can be perfumed with the aminoplast capsules of the invention, without observing significant leakage of the perfume during storage of the products.

Other pertinent documents in this context, cited earlier, are the detergent compositions described in detail in U.S. Pat. No. 5,480,575, to Lever Brothers, which enouces the basic components of this type of product, US 2004/0209793 to D. Fragonese, relating to liquid laundry detergents comprising ingredients capable of cross-linking with specific water-soluble polymers, or yet US 2001/0001786 relating to bleach containing detergents.

Detergent compositions in the form of anhydrous liquids, gels or pastes, comprising pre-mixes of amine oxide surfactants with appropriate solvents therefore, are described in detail in US 2004/0018953, to Procter & Gamble. These single dose dispensed compositions are also suitable for the purpose of the present invention, as are the laundry wash examples discussed in US 2003/0148908 to J. Michel et al., which relates to isotropic liquid detergents for laundry wash, packaged in polyvinyl alcohol (PVA) water soluble film.

The water-free cleaning compositions for manual detergents intended for use in the cleaning of hard surfaces, namely dishwashing, are fully disclosed in U.S. Pat. No. 6,820,626, to Henkel. The contents of this document which relate to the formulation of these anhydrous, optionally glycerol-free detergents, conditioned in water soluble or dispersible polymer capsules, are hereby included by reference. Automatic dish-washing compositions in the form of anhydrous gels, suitable as the detergent compositions of the present invention comprising fragranced melamine capsules, are disclosed in US 2004/0067861, to Procter & Gamble.

Many recent patent publications relate to conditioner or softener compositions, mostly in water soluble single dosage form, for use in the rinse cycle of fabric washing machines.

Very representative examples of such compositions, as well as the particular packaging therefore, can be found in the following documents, the contents of which, as regards the formulation of the anhydrous softener and its conditioning in the water-soluble packaging, is hereby included by reference. Most of these documents contain useful teachings of single dosage products perfectly suitable for the purpose of the present invention.

U.S. Pat. No. 4,851,141, to Colgate-Palmolive, comprises an early description of nonaqueous fabric softener compositions suitable for the purpose of the present invention.

International publication WO 02/102955, to Unilever, relates to single dose packaging of substantially non-aqueous liquid rinse conditioning compositions and comprises a detailed description of the ingredients which are typical in the latter. We enclose such teachings herein by reference.

Previously cited Procter & Gamble documents "840" and "841" comprise very detailed descriptions of two different types of fabric softeners which are also convenient for the purpose of the present invention, possibly delivered in the form of water-soluble unit dose pouches.

U.S. Pat. No. 6,492,315, to Colgate, is another pertinent example in this context, as are the US publications of the same company under U.S. Pat. Nos. 6,495,503 and 6,495,504. They all teach typical non-aqueous liquid fabric softeners in water soluble containers.

Finally, the already cited Procter & Gamble International application WO 00/66704 describes other prior art of pertinence with regard to the physical stability of heavy duty non-aqueous liquid detergents and comprises a very detailed description thereof, amongst other types of laundry detergents, wherein the heavy solids typically contained in such heavy duty detergents can be incorporated in microspheres allowing for physical stabilisation of the detergent. The laundry compositions of this type described in this document are also hereby included by reference.

Generally speaking, the invention relates to any liquid detergent or conditioner rinse off composition of the non-aqueous type, comprising less than 10% by weight of water or water-based solvents, known in the prior art, to which there can be added perfumed aminoplast capsules. The latter have surprisingly been found to remain stable over longer periods of time in these products than in aqueous products of similar function.

According to preferred embodiments of the invention, there will be provided non-aqueous liquid detergents and softeners for the treatment of fabrics. Particularly useful forms thereof will comprise bleaching agents.

The Microcapsules

The perfumed microcapsules to be used according to the invention include any aminoplast resin fragrance-containing microcapsules of current use or which are described in the prior art. The preparation of these capsules typically involves forming a dispersion or emulsion of the fragrance in an aqueous solution of urea-formaldehyde or melamine-formaldehyde pre-condensate and then causing condensation of the pre-condensate under acid catalysis conditions to produce microcapsules. Fragrance containing microcapsules of this type have been typically used in paper and cardboard applications, in "scratch & sniff" type products, as well as applied to textiles and other surfaces, wherein they release the perfume when the capsules are ruptured.

In order to render such capsules more stable in media containing surfactant or softening agents, a large number of modifications to these basic aminoplast shells have been proposed in recent patent literature, namely by modifying the surface of the capsule via the use of a second polymer, in particular a cationic polymer. In the context of the present invention, suitable fragranced microcapsules can be obtained by any of these prior known methods and both coated (particularly via cationic polymer coating) and uncoated aminoplast microcapsules can be used for the purpose of the invention.

Now, while capsules based on the use of these polymers provide a good way of protecting volatile and labile ingredients such as perfuming compounds from degradation in certain media, for instance in an aqueous or bleach environment, their use in functional consumer products wherein the treating base of the product comprises a surfactant system has been very restricted heretofore, as they have proved to be unstable in such a medium. We have now established that this is not the case in anhydrous type products as described above.

There are many prior art reports of the preparation of the microcapsules. In this context, particular reference is made here to the publications of K. Dietrich and collaborators in Acta Polymerica, volume 40 (1989), pages 243, 325, and 683, and volume 41 (1990), pages 91 and following. The review article of these authors on pages 243 to 251 is particularly rich in the citation of the polymers that can be generally used to prepare these microcapsules, as well as the methods for their preparation.

The patent literature is also rich in examples of preparation of melamine-formaldehyde and urea-formaldehyde microcapsules of the appropriate type for use according to the invention. Particular reference is made here to an early patent granted to the Wiggins Teape Group Limited, i.e. U.S. Pat. No. 4,396,670, which describes in detail many preparation examples of capsules suitable for the invention. We hereby include the teachings of this document by reference, as many of the capsules tested in the context of the invention were prepared using amine polymers of the type cited in this reference, namely in Examples 1 and 5.

Other patent literature of particular pertinence for the manufacture of the melamine capsules includes U.S. Pat. No. 3,516,941 and U.S. Pat. No. 4,976,961 (Minnesota Mining Co.), U.S. Pat. Nos. 4,406,816 and 6,224,795 (BASF), WO Patent 01/51197 or U.S. Pat. No. 6,719,931 (BASF) and U.S. Pat. No. 6,261,483 (BASF), WO 98/28396 or U.S. Pat. No. 6,194,375, to Quest International, in particular. All the described methods will provide capsules susceptible of being used according to the invention.

It is also described in the prior art that cationic transfer agents drive the deposition of such aminoplast capsules on fabric, skin and hair. This is of particular importance when such aminoplast capsules are used in liquid rinse-off formulations like laundry detergents, fabric conditioners, shampoos, rinse-off hair conditioners and body washes.

In this context, U.S. Pat. No. 4,234,627, assigned to Procter & Gamble, discloses a liquid fragrance coated with an aminoplast shell further coated by a water insoluble meltable cationic coating in order to improve the deposition of capsules from fabric conditioners. In U.S. Pat. No. 4,973,422 (P&G), from 1989, it was then further described that capsules with a cationic coating provide improved substantivity to the surface being treated, such as fabric treated with a fabric softener. The same idea was described in 1991 in U.S. Pat. No. 5,185,155, assigned to Unilever, where the selection of cationic polymers was enlarged to water soluble polymers and the type of encapsulation was distinct from those in the state of the art at the time. Patent application US 20040071742, assigned to IFF, discloses a similar technology where the fragranced aminoplast capsules are coated with cationic starch or cationic guar. International patent application WO 03/002699, assigned to Colgate-Palmolive, describes fabric softening compositions where a cationic cross-linked polymer improves deposition of friable aminoplast microcapsules. The improved deposition of cationic microcapsules in rinse-off formulations is also generally disclosed in US Patent application 2003/0171246, assigned to BASF, and International patent application WO 01/62376, assigned to Henkel. The descriptions of the nature and manufacture of all such microcapsules in these documents is hereby included by reference.

The present invention thus also includes coated aminoplast microcapsules prepared according to any of the methods described in these documents.

Such "cationic coated" melamine fragrance microcapsules may be the result of the incorporation of classical melamine based capsules in products comprising cationic transfer agents, which will inevitably lead to stabilisation of the capsules by a cationic sort of coating surrounding the original uncoated melamine capsule, or may be prepared separately via the use of cationic polymers and then incorporated in the end product. The prior art cited here-above includes examples of both types of coated melamine microcapsules and the scope of the present invention extends to the use of all such examples of melamine based fragrance microcapsules.

We have in fact unexpectedly established that the melamine microcapsules are further stabilized in the non-aqueous liquid detergents and softeners of the invention when "coated" with cationic compounds or polymers of the type mentioned in the above-cited documents. This cationic "coating" further prevents leakage of the fragrance in the non-aqueous liquids according to the invention.

Although prior attempts to increase the stability of such fragranced aminoplast capsules in aqueous liquids, by modifying the capsules' membrane, were reported for example in International patent application WO 02/074430, to Quest International, there was never any report or suggestion of the unexpected advantages of using conventional and cationic melamine based capsules in non-aqueous, possibly bleach-containing liquid detergents and softeners. The advantage of being able to use fragrance capsules which are stable in bleaches is obvious.

The Applicant has also previously addressed this issue in published International application WO 2005/017085, derived from PCT/IB03/03601, filed Aug. 13, 2003, wherein there is proposed a solution to the above-mentioned problem via the use of a special packaging system comprising two compartments, the fragranced aminoplast capsules being lodged in a compartment which is separate from that which contains the surface-active ingredients commonly present in such rinse-off formulations. The microcapsules there-described, which resort to the use of water soluble or dispersible polymers, are hereby included by reference.

Melamine resin capsules present many advantages when used as encapsulating systems for perfuming ingredients in application, i.e. in consumer products. First of all, when they break during use, for instance by friction, a fresh fragrance burst is perceived. On the other hand, when especially treated, these capsules are susceptible of being efficiently laid down on a surface during their use in an application. Therefore, when a surface is treated with a product according to the invention, the perfumed capsules settle on said surface, typically a textile, the skin or yet hair, depending on the nature of the surfactant-containing product, and provide an efficient release, by simple mechanical action such as a friction on the surface, of the perfuming ingredients encapsulated therein. These effects are optimal when the capsules are delivered in the non-aqueous liquid products of the invention.

In preferred embodiments of the invention, the fragranced microcapsules consist of melamine resin microcapsules. Suitable capsules for the purpose of the invention are also commercially available by manufacturers such as BASF (under the tradename of Micronal®). Typically, these capsules will encapsulate from 20 to 85% by weight of perfume, relative to their total weight.

The fragranced melamine resin capsules can be used in the form of a liquid aqueous suspension or dispersion. However, the capsules may also be used in the form of a dried powder, obtained after a drying treatment of a liquid suspension, e.g. via a spray-drying treatment carried out in a generally known manner or granulation with a suitable solid carrier. When used in an aqueous suspension, care must be taken to ensure that the water content in the final product remains within the limits indicated previously.

Particular attention is drawn to the microcapsules that can be obtained according to the processes, and using the raw materials, described in U.S. Pat. No. 4,396,670, to the Wiggins Teape Group Ltd. It has in fact been observed that such microcapsules, and the possibly cationic coated versions thereof, showed particular advantages over other classical melamine capsules in that they were capable of slight diffusion of the fragrance in the absence of any mechanical rubbing action. This means that such microcapsules, when transferred to the fabrics upon treatment thereof with the substantially anhydrous detergents and/or softeners in which they are incorporated, will provide slow diffusion of the fragrance from the fabrics, in addition to sudden bursts of said fragrance upon rupturing by natural body friction or rubbing.

The same effect was surprisingly observed with the abovementioned commercial microcapsules of BASF (prepared according to the methods described in WO 01/051197 A1) when such capsules were submitted to a "soft" heating treatment under mild temperature and duration conditions. The examples presented further on illustrate the manner in which such preferred melamine resin capsules can be prepared. The invention thus also relates to this preferred embodiment of the fragranced microcapsules of melamine resins and to the methods for their preparation, as well as to the liquid non-aqueous products containing such capsules. A preferred use method of the invention is thus a method of treatment of fabrics which includes the washing or rinsing thereof with non-aqueous liquid detergents and softeners containing such capsules.

Typically, these capsules have a perfume load comprised between 20 and 95% by weight, preferably between 50 and 95% and most preferably between 70 and 95%, relative to their total weight.

The concentration of microcapsules in the non-aqueous liquids of the invention will be such as to ensure a fragrance concentration in the product which is typically comprised between 0.01 and 10% by weight, more preferably from 0.05 to 5% by weight, more preferably from 0.1 to 2% by weight, relative to the total weight of the product.

The Fragrance

The microcapsules of the invention may contain any fragrance that one desires to encapsulate, provided that it is compatible with the materials forming the capsules. It will be typically chosen as a function of the perfuming effect that is desired to achieve with the consumer product of the invention, and it will be formulated according to current practices in the art of perfumery. It may consist of a perfume ingredient or of a composition. These terms can define a variety of odorant materials of both natural and synthetic origin, currently used for the preparation of perfumed consumer products. They include single compounds or mixtures. Specific examples of such components may be found in the current literature, e.g. Perfume and Flavor Chemicals by S. Arctander 1969, Montclair, N.J. (USA). These substances are well known to the person skilled in the art of perfuming consumer products, i.e. of imparting an odor to a consumer product traditionally fragranced, or of modifying the odor of said consumer product.

Natural extracts can also be encapsulated into the system of the invention; these include e.g. citrus extracts such as lemon, orange, lime, grapefruit or mandarin oils, or essentials oils of plants, herbs and fruits, amongst other.

Other examples of fragrances specifically formulated for melamine type capsules may be found in the patent literature, for example in WO 02/074430 to Quest International or in US 2004/071742, US 2004/071746 and US 2004/072719. The fragrance should be essentially free of water-miscible materials and, should it contain solvents, it will preferably contain such solvents as diethyl or dibutyl phthalate or, more preferably isopropyl myristate, as is taught in the above Quest document. The perfume may also contain other ingredients.

In more recent International documents assigned to Procter & Gamble, i.e. WO 2003/089561 and particularly WO 2005/002526, the preferred use of isopropyl myristate already disclosed in the above-cited Quest document is further confirmed. WO 2005/002526, in particular, teaches perfume compositions containing stabilizers which help improve the stability of a great variety microcapsules. The preferred such stabilizer is isopropyl myristate, but other substances are also cited. We hereby include by reference the pertinent teachings of these documents.

Our own studies during the development of the present invention have allowed us to establish that preferred embodiments of it relate to non-aqueous liquid products comprising melamine resin microcapsules in which there is encapsulated a perfume formulated according to certain principles, based on particular parameters of the perfumery raw materials. As far as the use of aminoplast microcapsules, melamine-formaldehyde capsules in particular, in these applications is concerned, we have established that perfumes containing large amounts of low Clog P substances (calculated log P; the calculation method used was that of Suzuki; according to Suzuki T. 1992, CHEMICALC 2, QCPE Program No 608, Department of chemistry, Indiana University; Suzuki T., Kudo Y. J. Comput.-Aided Mol. Design 1990, 4, 155; Suzuki T., J. Comput.-Aided Mol. Design 1991, 5, 149) and/or of substances having a volatility above 50 µg/L, are more likely to leak out of the capsules, upon application, than compositions having considerable concentration of substances which combine a Clog P of at least 3.5 with a volatility not above 50 µg/L.

Moreover, the Clog P and volatility of the end perfume may be controlled by diluting it with a very hydrophobic substance. Thus using one or more perfumery raw materials with Clog P above 5, will also help improve the stability of the perfume on application. Amongst the hydrophobic substances that can be used according to the invention, there can be cited raw materials such as Galaxolide®, Tonalide®, more preferably Habanolide® and, even more preferably isopropyl myristate. The concentration of such ingredients in the overall fragrance is at least 1% by weight, more preferably between 5 and 30% by weight, but may even reach 50% or more of the weight of the total fragrance.

The Packaging

The consumer products of the invention can be packaged in any form which is current for the packaging of known such consumables. Bottle containers may be made of various materials. Typically, they are made of plastics such as PET, OPP, PE or polyamide and including mixtures, laminates or other combinations of these.

These products can in particular and advantageously be packaged in pouches, sachets or other unit dosage packaging made of a water-soluble materials, in a single compartment or in generally known multiple compartment packages, such as those described for example in the prior patent literature cited previously in this description in the section devoted to the non-aqueous liquid consumer products of the invention. Single dose units of water-soluble films and pouches containing the consumer products, namely bleach containing such liquids, are preferred embodiments of the invention. The manner of their production has been described in much of the above-cited patent literature and is generally know to the skilled person.

Although the products of the invention do not require this, it is also clear that the consumer products of the invention can also be packaged as generally described in published International patent application WO 2005/01705, assigned to the Applicant and hereby included by reference. The latter essentially describes a multi-compartment package for a consumer product of the above-mentioned type wherein the dispersion of aminoplast or coacervate capsules and the surfactant-containing treating base can be lodged in separate compartments of the package, so as to optimise the storage stability. Typically, the package comprises two compartments of more-or-less comparable volume.

The invention will now be described in greater detail by way of the following examples wherein the temperatures are indicated in degrees Celsius and the abbreviations have the usual meaning in the art.

DETAILED EMBODIMENTS OF THE INVENTION

Example 1

Perfume Compositions

Perfume compositions intended for encapsulation in melamine resin capsules were prepared by admixing the following ingredients, in the proportions indicated.

| Perfume A | |
|---|---|
| Ingredient | Parts |
| Ethyl 2-methylbutanoate | 8.5 |
| Ethyl 2-methylpentanoate [1] | 8.5 |
| Dihydromyrcenol | 8.5 |
| Zestover | 8.5 |
| Allyl heptanoate | 8.5 |
| Delta-damascone [1] | 8.5 |
| Allyl cyclohexylpropionate | 8.5 |
| Violette BC [1] | 8.5 |
| Undecalactone | 8.5 |
| Hexyl salicylate | 8.5 |
| Tonalide | 15 |
| Total parts | 100 |

[1] Origin: Firmenich SA, Geneva, Switzerland;

| Perfume B | |
|---|---|
| | Parts |
| Ethyl 2-methylbutanoate | 9 |
| Ethyl 2-methylpentanoate [1] | 9 |
| Dihydromyrcenol | 9 |
| Zestover | 9 |
| Allyl heptanoate | 9 |
| Delta-damascone | 9 |
| Allyl cyclohexylpropionate | 9 |
| Violette BC | 9 |
| Undecalactone | 9 |
| Hexyl salicylate | 9 |
| Isopropyl myristate | 10 |
| Total parts | 100 |

[1] Origin: Firmenich SA, Geneva, Switzerland;

Example 2

Preparation of Microcapsules

Microcapsules were prepared with a commercially available etherified melamine-formaldehyde (MF) resin, using the ingredients cited below, in the concentrations indicated, and following the preparation method described here-below.

| Ingredient | Amount (g) |
|---|---|
| MF resin (*) | 39.50 |
| Colloidal stabilizer (**) | 7.50 |
| Water | 222.50 |
| Perfume (***) | 230.00 |
| Acetic acid | 5.45 |
| Urea | 10.00 |
| Ammonia solution 25% | 4.50 |
| Total | 519.45 |

(*) Luracoll VFR 70% in aqueous solution, origin: BASF
(**) Copolymer of acrylamide and acrylic acid, origin: Aldrich
(***) The perfume used can be any one of those described in example 1 or any other perfume created according to the desired perfuming effect; preferred perfumes used obeyed the constraints defined in the general description above Experimental Procedure:

In a 500 ml reactor, the colloidal stabilizer was added to the MF solution under high shear (1000 RPM) conditions. Then the perfume was added at room temperature. The resulting emulsion had a pH value of 7.3. The desired pH value for the poly-condensation process was obtained by adding the necessary amount of acetic acid. In the present case the pH value was about 4.6. The reaction mixture was then heated to 50° C. and kept at this temperature for one hour. Then the temperature was increased to 60° C. and the shear rate reduced to less than 400 RPM. The reaction mixture was kept under these conditions for 3 hours. To reduce the free formaldehyde concentration, a pre-determined amount of urea was added to the capsule suspension and the latter was kept under the same shear rate and temperature for one hour more. After cooling to room temperature the pH of this capsule suspension was raised to a value between 7 and 8.

The mean size of capsules was determined by optical microscopy and light scattering techniques and found to be equal to 30 μm. The final perfume content in the suspension was about 44%. The capsules were able to slightly diffuse the fragrance even without rupturing the capsules by rubbing.

Other microcapsules were prepared in a similar manner, but varying the nature of the melamine-formaldehyde resin and colloidal stabilizer, or yet according to prior known techniques, many of which are described in the literature already cited, but varying the nature of the melamine-formaldehyde resin and colloidal stabilizer. All such capsules were suitable for incorporation in the non-aqueous liquid products according to the invention.

Example 3

Preparation of a Liquid Anhydrous Laundry Detergent Comprising Microcapsules and Comparison of its Stability with that of a Liquid Aqueous Laundry Detergent Containing Identical Microcapsules Melamine-formaldehyde microcapsules comprising the Perfume A disclosed in example 1 were prepared as is described in BASF patent application WO 01/51197 A1. The capsules (corresponding to 0.5% encapsulated perfume A in finished product) were then incorporated in a commercial concentrated aqueous detergent of the Persil® UK Concentrated (tradename of Unilever) type, having the following essential ingredients as indicated in the package information, to prepare Comparative Aqueous Liquid Detergent A.

| Ingredients | Amount |
| --- | --- |
| Polycarboxylates, Phosphonates | Less than 5% |
| Non-ionic surfactants, Soap | 5-15% |
| Anionic surfactants | 15-30% |
| Also contains enzyme and preservatives | Minor |
| Water | 60% |

Incorporation of the same capsules, at the rate of 0.5% encapsulated perfume A in finished product, in an aqueous (53% water content) detergent of the Tide® Free (tradename of Procter & Gamble), the composition of which is indicated on the package as being covered by U.S. Pat. Nos. 4,537,707; 4,550,862; 4,561,998; 4,597,898; 4,968,451; 5,565,145; 5,929,022; 6,294,514 and 6,376,445, provided Comparative Aqueous Liquid Detergent B.

A novel Anhydrous Liquid Detergent 1 was prepared by incorporating the same microcapsules, at the rate of 1% encapsulated perfume A in finished product, in an anhydrous commercial detergent of the Persil Liquigel (tradename of Unilever) type, packaged in PVOH sachets and having the following basic composition:

| Ingredients | Amount |
| --- | --- |
| Phosphonates | Less than 5% |
| Anionic surfactants, Non-ionic surfactants, Soap | 15-30% |
| Also contains enzyme and brightening agents | Minor |
| Water | 6% |

The stability of the microcapsules in the four detergent samples thus prepared, as measured by the sum of the amount of leakage of each perfume raw material (PRM) over time was evaluated.

To this effect, 2 g of finished product were placed in a 10 ml vial, diluted with 6 ml ethyl acetate and quickly mixed by hand for 30 seconds. The resulting mixture was quickly filtered on a disposable filter (0.4 microns pores) to remove any suspended microcapsules. The filtrate was left to settle and the ethyl acetate top layer was dried and then analysed by GC-MS. The results of the evaluation are presented in the table below.

TABLE 1

Perfume leakage from fragrance microcapsules incorporated in detergent

| Sample | Total % of perfume leakage after 3 day storage at 37 C. |
| --- | --- |
| Comparative Aqueous Liquid Detergent A | 52 |
| Comparative Aqueous Liquid Detergent B | 54 |
| Anhydrous Liquid Detergent 1 | 10 |

The results summarized in this Table clearly show that the Anhydrous Liquid Detergent according to the invention is unexpectedly and advantageously stable over the Aqueous Liquid Detergents of the prior art.

Example 4

Preparation of a Liquid Anhydrous Laundry Detergent Comprising Microcapsules and Comparison of its Stability with that of a Liquid Aqueous Laundry Detergent Containing Identical Microcapsules Melamine-formaldehyde microcapsules comprising the Perfume A disclosed in Example 1 were prepared as is described in Example 2.

The capsules (corresponding to 0.5% weight of encapsulated perfume A in finished product) were then incorporated in a commercial concentrated aqueous detergent of the Persil® UK Concentrated (tradename of Unilever) type, having the following essential ingredients as indicated in the package information, to prepare Comparative Aqueous Liquid Detergent A.

| Ingredients | Amount |
| --- | --- |
| Polycarboxylates, Phosphonates | Less than 5% |
| Non-ionic surfactants, Soap | 5-15% |
| Anionic surfactants | 15-30% |
| Also contains enzyme and preservatives | Minor |
| Water | 60% |

Incorporation of the same capsules, at the rate of 0.5% encapsulated perfume A in finished product, in an aqueous (53% water content) detergent of the Tide® Free (tradename of Procter & Gamble), the composition of which is indicated on the package as being covered by U.S. Pat. Nos. 4,537,707; 4,550,862; 4,561,998; 4,597,898; 4,968,451; 5,565,145; 5,929,022; 6,294,514 and 6,376,445, provided Comparative Aqueous Liquid Detergent B.

A novel Anhydrous Liquid Detergent 1 was prepared by incorporating the same microcapsules, at the rate of 1% encapsulated perfume A in finished product, in an anhydrous commercial detergent of the Persil Liquigel (tradename of Unilever) type, packaged in PVOH sachets and having the following basic composition:

| Ingredients | Amount |
| --- | --- |
| Phosphonates | Less than 5% |
| Anionic surfactants, Non-ionic surfactants, Soap | 15-30% |
| Also contains enzyme and brightening agents | Minor |
| Water | 6% |

The stability of the microcapsules in the four detergent samples thus prepared, as measured by the sum of the amount of leakage of each perfume raw material (PRM) over time, was evaluated, following the protocol described in Example 3. The results of the evaluation are presented in the table below.

TABLE 2

Perfume leakage from fragrance microcapsules incorporated in detergent

| Sample | % of perfume leakage after 3 day storage at 37 C. | % of perfume leakage after 14 day storage at 37 C. |
| --- | --- | --- |
| Comparative Aqueous Liquid Detergent A | 69 | |
| Comparative Aqueous Liquid Detergent B | 63 | |
| Anhydrous Liquid Detergent 1 | 10 | 23 |

The results summarized in this Table clearly show that the Anhydrous Liquid Detergents according to the invention is unexpectedly and advantageously stable over the Aqueous Liquid Detergents of the prior art.

Example 5

Preparation of a Liquid Anhydrous Laundry Detergent Comprising Microcapsules and Comparison of its Stability with that of a Liquid Aqueous Laundry Detergent Containing Identical Microcapsules Melamine-formaldehyde microcapsules comprising the Perfume B disclosed in Example 1 were prepared as is described in Example 2.

The capsule (corresponding to 0.5% encapsulated perfume B in finished product) were then incorporated in a commercial concentrated aqueous detergent of the Persil® UK Concentrated (tradename of Unilever) type, having the following essential ingredients as indicated in the package information, to prepare Comparative Aqueous Liquid Detergent A.

| Ingredients | Amount |
| --- | --- |
| Polycarboxylates, Phosphonates | Less than 5% |
| Non-ionic surfactants, Soap | 5-15% |
| Anionic surfactants | 15-30% |
| Also contains enzyme and preservatives | Minor |
| Water | 60% |

Incorporation of the same capsules, at the rate of 0.5% encapsulated perfume B in finished product, in an aqueous (53% water content) detergent of the Tide® Free (tradename of Procter & Gamble), the composition of which is indicated on the package as being covered by U.S. Pat. Nos. 4,537,707; 4,550,862; 4,561,998; 4,597,898; 4,968,451; 5,565,145; 5,929,022; 6,294,514 and 6,376,445, provided Comparative Aqueous Liquid Detergent B.

A novel Anhydrous Liquid Detergent 1 was prepared by incorporating the same microcapsules, at the rate of 1% encapsulated perfume B in finished product, in an anhydrous commercial detergent of the Persil Liquigel (tradename of Unilever) type, packaged in PVOH sachets and having the following basic composition:

| Ingredients | Amount |
| --- | --- |
| Phosphonates | Less than 5% |
| Anionic surfactants, Non-ionic surfactants, Soap | 15-30% |
| Also contains enzyme and brightening agents | Minor |
| Water | 6% |

The stability of the microcapsules in the four detergent samples thus prepared, as measured by the sum of the amount of leakage of each perfume raw material (PRM) over time, was evaluated, following the protocol described in Example 3. The results of the evaluation are presented in the table below.

TABLE 3

Perfume leakage from fragrance microcapsules incorporated in detergent

| Sample | % of perfume leakage after 3 day storage at 37 C. | % of perfume leakage after 14 day storage at 37 C. |
| --- | --- | --- |
| Comparative Aqueous Liquid Detergent A | 80 | |
| Comparative Aqueous Liquid Detergent B | 45 | |
| Anhydrous Liquid Detergent | 9 | 37 |

The results summarized in this Table clearly show that the Anhydrous Liquid Detergents according to the invention is unexpectedly and advantageously stable over the Aqueous Liquid Detergents of the prior art.

Example 6

Evaluation of Olfactive Impact of Anhydrous Fabric Softener Containing Microcapsules The performance of the anhydrous liquid detergents of the invention on the treatment of fabrics was evaluated. Samples of anhydrous liquid detergents were used in conventional fabric washing machines, during the washing cycle of the fabric treatment. The treatment and evaluation conditions were as follows.

Anhydrous Liquid Detergent:

References without microcapsules: commercial detergents comprising 1% by weight of a non-encapsulated perfume (Comparative)

Test products with microcapsules: To the non-aqueous perfumed detergent base above were added microcapsules according to the invention comprising perfume A or B, in such a concentration that the weight of encapsulated perfume A or B in the softener was 0.3%, to obtain the Samples 1 to 3 according to the invention.

Washing Method

The wash consisted of 2 kg cotton fabric load treated with 2 capsules of the anhydrous detergent (recommended dosage, 50 g each). The fabrics were washed at 40° C. in Miele® European washing machines (short cycle, 1 h, total 49 l of water/wash). The cotton load was mostly made of 40 small cotton face towels (20 by 20 cm) used for evaluation by a sensory panel on blind tests. Washed face towels were line dried for 16 h, piled by 10 and loosely covered with aluminium foil for storage.

Evaluation Method

Three samples (Samples 1 to 3 according to the invention) of perfumed detergent (1% by weight of a free perfume), further comprising three different varieties of microcapsules according to the invention, all providing 0.3% by weight of encapsulated perfume A or B in the detergent, were used to treat fabrics. The latter (Fabrics 1 to 3) were compared, on a blind test, with the fabrics (Comparative) treated with the commercial anhydrous liquid detergent containing only 1% by weight of an un-encapsulated perfume.

The perfume intensity on dry fabrics was evaluated on a blind test by a 25 people panel, who were asked to judge, using an intensity scale of 1 to 7 (1 no odour, 4 medium odour, 7 very strong odour), the intensity of the fabrics odour, before and after rubbing the textiles.

The results of the evaluations are presented on the table below.

TABLE 4

Olfactive Impact of Anhydrous Liquid Detergents

| | Evaluation conditions | | | |
|---|---|---|---|---|
| | 1 day dry fabrics | | 3 day dry fabrics | |
| | Before rubbing | After rubbing | Before rubbing | After rubbing |
| Comparative A: 1% free perfume | 1.55 | 1.53 | 2.03 | 2.17 |
| Fabrics 1: treated with detergent containing 1% free perfume + 0.3% perfume A encapsulated as described in WO 01/51197 A1 | 1.80 | 4.09 | 2.00 | 3.64 |
| Fabrics 2: treated with detergent containing 1% free perfume + 0.3% perfume A encapsulated as in Example 2 | 3.38 | 5.19 | 3.10 | 5.15 |
| Fabrics 3: treated with detergent containing 1% free perfume + 0.3% perfume B encapsulated as in Example 2 | 3.13 | 4.71 | 2.75 | 4.20 |

Standard deviation: +/−0.5 points

The results above show that the fabrics perfumed with the anhydrous liquid detergents of the invention develop a consistently more intense odour than those washed with the prior known anhydrous detergent, both before and after rubbing.

Example 7

Preparation of a Liquid Anhydrous Fabric Softener Comprising Microcapsules and Comparison of its Stability and with that of a Liquid Aqueous Fabric Softener Containing Identical Microcapsules Melamine-formaldehyde microcapsules comprising the Perfume A disclosed in Example 1 were prepared as is described in BASF patent application WO 01/51197 A1. The capsules were then incorporated, at a concentration such that it provided 0.8% by weight of perfume A in the softener, in a conventional aqueous (more than 80% water by weight) fabric softener having the following essential ingredients, to prepare a Comparative Aqueous Softener.

| Ingredients | Amount |
|---|---|
| StepantexTM VS 90 diester quaternary ammonium salt (fabric-softener active) | 16.5% |
| Calcium Chloride | 0.2% |
| Water | 83.2% |

A novel Anhydrous Fabric Softener according to the invention was prepared by incorporating the same microcapsules, at the same concentration rate, in an anhydrous commercial product of the Comfort Pearls (tradename of Unilever) type, packaged in PVOH sachets and having the following basic composition:

| Ingredients | Amount |
|---|---|
| Phosphonates | Less than 5% |
| Non-ionic surfactants | 5-15% |
| Soap | 15-30% |
| Water | 3% |
| Hydrotropes | Balance to 100% |

The stability of the microcapsules in the two fabric softener samples thus prepared, as measured by the sum of the amount of leakage of each perfume raw material (PRM) over time, was evaluated, following the protocol described in Example 3. The results of the evaluation are presented in the table below.

TABLE 5

Perfume leakage from fragrance microcapsules incorporated in softener

| Sample | % of perfume leakage after 14 day storage at 37 C. | % of perfume leakage after 28 day storage at 37 C. |
|---|---|---|
| Comparative Aqueous Liquid Softener | 34.0 | |
| Anhydrous Liquid Softener | 0.9 | 1.2 |

The results summarized in this Table clearly show that the Anhydrous Liquid Fabric Softener according to the invention is unexpectedly and advantageously stable over the Liquid Aqueous Fabric Softener of the prior art.

Example 8

Evaluation of Olfactive Impact of Anhydrous Fabric Softener Containing Microcapsules The performance of the anhydrous liquid fabric softener of the invention cited in Example 7 on the treatment of fabrics was evaluated, both immediately after preparation of the softener and after 1 and 2 months storage. Samples of the fabric softener were used in conventional fabric washing machines, during the rinse cycle of the fabric treatment. The treatment and evaluation conditions were as follows.

Washing Method

The wash consisted of 1.8 kg cotton fabric load treated with 85 grams of unperfumed detergent plus one capsule of fabric softener (recommended dosage, 25 g). Fabrics were washed at 40° C. in Miele® European washing machines (short cycle, 1 h, total 49 l of water/wash). The cotton load was mostly made of 40 small cotton face towels (20 by 20 cm) used for evaluation by a sensory panel on blind tests. Washed face towels were line dried for 16 h, piled by 10 and loosely covered with aluminium foil for storage.

Evaluation

A liquid anhydrous fabric softener sample according to Example 7, comprising 0.8% by weight of perfume A encapsulated in the microcapsules according to the invention, was used to treat fabrics and the latter were compared with the fabrics (Comparative) treated with the same anhydrous softener but which contained only the same concentration of free perfume A.

The perfume intensity on dry fabrics was evaluated on a blind test by a 25 people panel, who were asked to judge, using an intensity scale of 1 to 7 (1 no odour, 4 medium odour, 7 very strong odour), the intensity of the fabrics odour, before and after rubbing the textiles.

TABLE 6

Olfactive Impact of Anhydrous Softeners, Freshly Made and After Storage

| | 1 day dry fabrics Fabric softener status | | | | | |
|---|---|---|---|---|---|---|
| | Freshly made | | 1 month at 37 C. | | 2 months at 37 C. | |
| | Before rubbing | After rubbing | Before rubbing | After rubbing | Before rubbing | After rubbing |
| Comparative fabrics | 1.90 | 2.10 | 1.94 | 2.13 | 2.09 | 2.20 |
| Fabrics treated with softener of the invention | 3.68 | 6.00 | 4.19 | 6.09 | 3.40 | 5.63 |

Standard deviation: +/−0.5 points

The results above show that the fabrics perfumed with the anhydrous softener of the invention develop a consistently more intense odour than those washed with the prior known anhydrous softener, both before and after rubbing.

Example 9

Preparation of a Liquid Anhydrous Fabric Softener Comprising Microcapsules and Evaluation of its Stability and Olfactive Impact A. Stability Melamine-formaldehyde microcapsules comprising the Perfume A disclosed in Example 1 were prepared as is described in Example 2.

The capsules were then incorporated, at a concentration providing 0.8% by weight of perfume A in the softener, in a conventional aqueous (more than 80% water by weight) fabric softener having the following essential ingredients, to prepare a Comparative Aqueous Softener.

| Ingredients | Amount |
|---|---|
| StepantexTM VS 90 diester quaternary ammonium salt (fabric-softener active) | 16.5% |
| Calcium Chloride | 0.2% |
| Water | 83.2% |

A novel Anhydrous Fabric Softener according to the invention was prepared by incorporating the same microcapsules, at the same concentration rate, in an anhydrous commercial product of the Comfort Pearls (tradename of Unilever) type, packaged in PVOH sachets and having the following basic composition:

| Ingredients | Amount |
|---|---|
| Phosphonates | Less than 5% |
| Non-ionic surfactants | 5-15% |
| Soap | 15-30% |
| Water | 3% |
| Hydrotropes | Balance to 100% |

The stability of the microcapsules in the two fabric softener samples thus prepared, as measured by the sum of the amount of leakage of each perfume raw material (PRM) over time, was evaluated, following the protocol described in Example 3. The results of the evaluation are presented in the table below.

TABLE 7

Perfume leakage from fragrance microcapsules incorporated in softener

| Sample | % of perfume leakage after 14 day storage at 37 C. | % of perfume leakage after 28 day storage at 37 C. |
|---|---|---|
| Comparative Aqueous Liquid Softener | 63 | |
| Anhydrous Liquid Softener | 10 | 20 |

Standard deviation: +/−0.5 points

The results summarized in this Table clearly show that the Anhydrous Liquid Fabric Softener according to the invention is unexpectedly and advantageously stable over the Liquid Aqueous Fabric Softener of the prior art.

B. Olfactive Impact

The performance of the anhydrous liquid fabric softener of the invention cited above on the treatment of fabrics was evaluated, both immediately after preparation of the softener and after 1 and 2 months storage. The treatment of the fabrics and their evaluation were carried out as is described in Example 8. The Comparative fabric softener comprised 0.96% by weight of free perfume A and the anhydrous fabric softener of the invention comprised perfumed microcapsules providing the same amount of perfume A in the softener.

The results of the evaluations, summarized in Table 8, showed consistently better odour performance from the fabrics treated with the anhydrous liquid softener of the invention.

TABLE 8

Olfactive Impact of Anhydrous Softeners, Freshly Made and After Storage

| | 1 day dry fabrics Fabric softener status | | | | | |
|---|---|---|---|---|---|---|
| | Freshly made | | 1 month at 37 C. | | 2 months at 37 C. | |
| | Before rubbing | After rubbing | Before rubbing | After rubbing | Before rubbing | After rubbing |
| Comparative fabrics | 1.98 | 2.20 | 1.86 | 2.10 | 1.70 | 2.40 |
| Fabrics treated with softener of the invention | 4.58 | 5.96 | 4.50 | 4.64 | 3.81 | 3.96 |

The invention claimed is:

1. A liquid substantially non-aqueous detergent composition, comprising a fragrance encapsulated in aminoplast microcapsules, a surfactant present in an amount of between 20 and 45% by weight, relative to the weight of the composition, and a water content which is not above 6% by weight, relative to the total weight of the composition; with the composition being free of fabric softeners and in the form of a product selected from the group consisting of a liquid detergent, a shampoo, a liquid soap, a shower gel, or a liquid all-purpose cleaner.

2. The composition according to claim 1, wherein the microcapsules are obtained from a melamine-formaldehyde condensation reaction.

3. The composition according to claim 2, wherein the microcapsules carry a cationic coating thereon.

4. The composition according to claim 3, wherein the cationic coating is a cationic polymer coating.

5. The composition according to claim 1, wherein the encapsulated perfume is present in an amount of between 0.01 and 10% by weight of the total weight of the composition.

6. The composition according to claim 5, wherein the encapsulated perfume is present in an amount of 0.05 to 5% by weight, relative to the weight of the composition.

7. The composition according to claim 5, wherein the perfume comprises at least 50% to 70% by weight of the total weight of perfume, of perfumery raw materials having a Clog P above 3.5 and a volatility below 50 μm/L.

8. The composition according to claim 1, containing from 20 to 45% weight, relative to the weight of the product, of the surfactant alone or in a surfactant system or a surfactant active ingredient system.

9. The composition according to claim 1, wherein the product further comprises a bleach.

10. The composition according to claim 1, wherein the product is contained in a single dose package.

11. The composition according to claim 10, wherein the package is formed of polyvinyl alcohol (PVOH) or a mixture thereof with another water-soluble polymer.

12. A method for treating a surface which comprises applying a composition according to claim 1 onto the surface to be treated.

13. The method according to claim 12, wherein the surface to be treated is the surface of fabrics and the composition is a laundry detergent applied to fabrics by being added to a compartment of a washing machine for washing of the fabrics under normally known conditions so as to transfer the perfume onto the fabrics.

14. A method for treating a surface which comprises applying a single dose consumer product according to claim 10 onto the surface to be treated.

15. The method according to claim 14, wherein the surface to be treated is the surface of fabrics and the composition is a laundry detergent applied to fabrics by being added to a compartment of a washing machine for washing of the fabrics under normally known conditions so as to transfer the perfume onto the fabrics.

16. A liquid substantially non-aqueous cleaning composition, consisting essentially of a fragrance encapsulated in aminoplast microcapsules, wherein the encapsulated perfume is present in an amount of between 0.01 and 10% by weight of the total weight of the composition, a surfactant present in an amount of between 20 to 45% weight, relative to the weight of the composition, and being present alone or in a surfactant system or a surfactant active ingredient system, and a water content which is not above 6% by weight, relative to the total weight of the composition, with the composition being free of fabric softeners and in the form of a product of a detergent, a shampoo, a liquid soap, a shower gel, or a liquid all-purpose cleaner, the product being contained in a single dose package formed of polyvinyl alcohol (PVOH) or a mixture thereof with another water-soluble polymer.

\* \* \* \* \*